United States Patent
Nelson, Jr. et al.

(10) Patent No.: US 12,292,428 B2
(45) Date of Patent: *May 6, 2025

(54) RAPID, SENSITIVE HYDROGEN DETECTOR WITH ACTIVE HYDROGEN-DERIVED WATER VAPOR SIGNAL MODULATION

(71) Applicant: Aerodyne Research, Inc., Billerica, MA (US)

(72) Inventors: David D. Nelson, Jr., N. Chelmsford, MA (US); Scott C. Herndon, Littleton, MA (US); Joanne H. Shorter, Lexington, MA (US); Joseph R. Roscioli, Chelmsford, MA (US)

(73) Assignee: Aerodyne Research, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,818

(22) Filed: Dec. 14, 2022

(65) Prior Publication Data
US 2023/0116043 A1  Apr. 13, 2023

Related U.S. Application Data

(62) Division of application No. 17/178,696, filed on Feb. 18, 2021, now Pat. No. 11,802,858.

(51) Int. Cl.
*G01N 33/00* (2006.01)
(52) U.S. Cl.
CPC ....... *G01N 33/005* (2013.01); *G01N 33/0013* (2013.01); *G01N 33/0016* (2013.01)
(58) Field of Classification Search
CPC ............. G01N 33/005; G01N 33/0036; G01N 33/006; G01N 33/0059; G01N 33/0009;
(Continued)

(56) References Cited

U.S. PATENT DOCUMENTS 3,549,327 A  12/1970 Fergusson
6,897,960 B2  5/2005  DiMeo, Jr. et al.
(Continued)

FOREIGN PATENT DOCUMENTS

CN  201811870 U  *  4/2011
CN  111007031 A     4/2020
(Continued)

OTHER PUBLICATIONS

CN-201811870-U (Year: 2011).*
(Continued)

*Primary Examiner* — Kristina M Deherrera
*Assistant Examiner* — Fatemeh Esfandiari Nia
(74) *Attorney, Agent, or Firm* — Cesari and McKenna, LLP; James A. Blanchette (57) ABSTRACT

In various embodiments, rapid, sensitive detection of molecular hydrogen is achieved by chemically converting hydrogen to water vapor and then detecting the water vapor as a surrogate for the hydrogen. Detection may be enhanced by dampening variation in ambient water vapor and rapidly actively modulating a hydrogen-derived water vapor component. For example, the detector may receive sample gas that includes ambient water vapor and hydrogen, dry the sample gas to dampen variation in the ambient water vapor, divide the sample gas into a chemical conversion flow and a bypass flow, chemically convert hydrogen in the chemical conversion flow to water vapor, alternate between measuring water vapor in the converted chemical conversion flow or the bypass flow to produce a water vapor signal, separate the water vapor signal in the time domain to extract a hydrogen-derived water vapor signal, and output a hydrogen signal based on the hydrogen-derived water vapor signal.

20 Claims, 6 Drawing Sheets

(58) Field of Classification Search
CPC .......... G01N 33/0004; G01N 33/0016; G01N 21/3504; G01N 21/3554; G01N 1/44

See application file for complete search history.

(56) References Cited

U.S. PATENT DOCUMENTS

| | | | |
|---|---|---|---|
| 7,255,836 | B2 | 8/2007 | Lehmann et al. |
| 7,277,177 | B2 | 10/2007 | Augustine et al. |
| 7,852,480 | B2 | 12/2010 | Uchiyama |
| 8,448,493 | B2* | 5/2013 | McIntyre .......... G01N 30/7206 73/23.37 |
| 9,322,969 | B2 | 4/2016 | Burov et al. |
| 11,561,324 | B1 | 1/2023 | Burba |
| 2002/0154310 | A1 | 10/2002 | DiMeo, Jr. et al. |
| 2003/0082417 | A1 | 5/2003 | Lillis |
| 2004/0023595 | A1 | 2/2004 | Ping et al. |
| 2004/0107764 | A1 | 6/2004 | Yan |
| 2004/0193379 | A1* | 9/2004 | Lillis .................. H01M 16/003 702/102 |
| 2005/0272167 | A1* | 12/2005 | Andino ................ G01N 33/005 436/144 |
| 2007/0240488 | A1* | 10/2007 | Kreuser ............. G01N 33/0013 73/19.07 |
| 2011/0174052 | A1* | 7/2011 | Kuebel ................ G01N 33/005 73/23.31 |
| 2017/0023475 | A1 | 1/2017 | Dam et al. |
| 2017/0184537 | A1* | 6/2017 | Umasankar ........ G01N 27/4065 |
| 2019/0263699 | A1 | 8/2019 | Finger et al. |
| 2020/0033301 | A1 | 1/2020 | Cardin |
| 2021/0293768 | A1 | 9/2021 | Johnson et al. |
| 2022/0187203 | A1 | 6/2022 | Zondlo et al. |
| 2022/0260537 | A1 | 8/2022 | Nelson, Jr. et al. |

FOREIGN PATENT DOCUMENTS

| | | |
|---|---|---|
| CN | 108562017 B | 11/2020 |
| EP | 2140249 B1 | 9/2011 |
| GB | 1017940 A | 1/1966 |
| JP | S-49-026920 B1 | 7/1974 |
| JP | S60/80755 A | 5/1985 |
| JP | H07/325075 A | 12/1995 |
| JP | 2006/179224 A | 7/2006 |
| JP | 2011-257319 A | 12/2011 |
| JP | 6641218 B2 | 2/2020 |
| WO | WO2011/155086 A1 | 12/2011 |

OTHER PUBLICATIONS

CN-108562017-B-eng (Year: 2020).

JP-6641218-B2-eng (Year: 2020).

Chtanov, A., et al., "Differential Optical Detection of Hydrogen Gas in the Atmosphere," Elsevier Sciences B.V., Elsevier, Sensors and Actuators, vol. 79, Issue 2-3, Oct. 15, 2001, pp. 196-199.

"HALO H2: Trace-Level Hydrogen Analyzer," Tiger Optics, Tiger Optics, LLC, May 2020, pp. 1-2.

"HALO H2: Trace-Level Hydrogen Analyzer," Tiger Optics, Tiger Optics, LLC, Oct. 2021, pp. 1-2.

L'Vov, Boris V., et al., "Catalytic Oxidation of Hydrogen on Platinum," Springer, Akadémiai Kiadó, Budapest Hungary, Journal of Thermal Analysis Calorimetry, Sep. 7, 2012, pp. 1-8.

"Notification of Transmittal of the International Search Report and the Written Opinion of the International Searching Authority, or the Declaration," International Filing Date: Jan. 27, 2022, International Application No. PCT/US2022/014073, Applicant: Aerodyne Research, Inc., Date of Mailing: Jun. 21, 2022, pp. 1-19.

Rizzolo, Serena, et al., "Distributed and Discrete Hydrogen Monitoring Through Optical Fiber Sensors Based on Optical Frequency Domain Reflectometry," IOP Publishing Ltd, JPhys Photonics, vol. 2, Jan. 28, 2020, pp. 1-7.

Rollins, A. W., et al., "Catalytic Oxidation of $H_2$ on Platinum: A robust Method for Generating Low Mixing Ratio $H_2O$ Standards," Copernicus Publications, Atmospheric Measurement Techniques, vol. 4, Oct. 4, 2011, pp. 2059-2064.

Shin, Woosuck et al., "Hydrogen-Selective Thermoelectric Gas Sensor", Sensors and Actuators B: Chemical, Elsevier B.V., NL, vol. 93, No. 1-3, Aug. 1, 2003, pp. 304-308.

Shin, Woosuck et al., "Integration of Ceramic Catalyst on Micro-Thermoelectric Gas Sensor", Sensors and Actuators B: Chemical, Elsevier B.V., NL, vol. 118, No. 1-2, Oct. 25, 2006, pp. 283-291.

"Notification of Transmittal of the International Search Report and the Written Opinion of the International Searching Authority, or the Declaration," International Filing Date: Oct. 31, 2023, International Application No. PCT/US2023/036493, Date of Mailing: Feb. 26, 2024, pp. 1-12.

\* cited by examiner

RAPID, SENSITIVE HYDROGEN DETECTOR WITH ACTIVE HYDROGEN-DERIVED WATER VAPOR SIGNAL MODULATION

RELATED APPLICATIONS

The present application is a divisional of U.S. patent application Ser. No. 17/178,696, filed on Feb. 18, 2021, by David D. Nelson, Jr. et al for a "Rapid, Sensitive Hydrogen Detector", now issued as U.S. Pat. No. 11,802,858, the contents of which are incorporated by reference herein in their entirety.

BACKGROUND

Technical Field

The present disclosure relates generally to gas detection, and more particularly to rapid, sensitive detection of molecular hydrogen.

Background Information

There is a growing need for rapid, sensitive detection of molecular hydrogen. As the world transitions away from fossil fuels as our primary energy source, it is likely that a hydrogen-based energy infrastructure will emerge. Both for economic and safety reasons it will be essential to have effective ways of measuring hydrogen concentration. For example, to detect hydrogen gas leaks it will be essential to have effective ways of measuring hydrogen concentration in sample gas (e.g., atmospheric air). Just as methane detectors play an important role in our existing natural gas-based energy infrastructure, hydrogen detectors will likely play an important role in hydrogen-based energy infrastructure.

Many currently deployed methane detectors utilize optical detection to measure methane concentration and detect methane gas leaks. Optical detection can be fast, sensitive, portable, and specific, and it would seemingly be an appealing option for use in detecting hydrogen. However, unlike methane, hydrogen has no strong absorption features in the near ultraviolet (UV), visible, infrared (IR) or microwave regions of the electromagnetic spectrum. Accordingly, it is very difficult to optically detect hydrogen molecules with conventional techniques and direct optical detectors for hydrogen have not proved viable.

Accordingly, there is a need for improved techniques for detecting molecular hydrogen that may enable rapid, sensitive hydrogen detection.

SUMMARY

In various embodiments, rapid, sensitive detection of molecular hydrogen is achieved by chemically converting hydrogen to water vapor (i.e., oxidizing the hydrogen) and then optically detecting the water vapor (e.g., using an optical detection technique such as laser spectroscopy, non-dispersive infrared (NDIR) absorption spectroscopy, etc.). The water vapor serves as a surrogate for hydrogen, such that hydrogen is indirectly detected. Indirect detection avoids the difficulties of optically detecting hydrogen molecules themselves and may provide other advantages. However, indirect detection may also introduce other challenges. In various embodiments described herein, these other challenges may be addressed.

One challenge is that the sample gas (e.g., atmospheric air) often includes significant ambient water vapor (e.g., 1% to 4%). The additional water vapor produced by chemically converting hydrogen will typically be very small compared to the ambient water vapor. Even when detecting nearby a hydrogen leak it may be hundreds of times smaller, and if remote from a hydrogen leak it may be tens of thousands of times smaller. In addition, the amount of ambient water vapor may change with time, and be correlated with air movements, causing further problems in specific detection.

In various embodiments described herein, this challenge may be addressed by separating a water vapor signal describing detected water vapor concentration into two components in the time domain, referred to as the "ambient water vapor signal" and the "hydrogen-derived water vapor signal." Separation may be facilitated by dampening variation in the ambient water vapor signal to differentiate it from the more rapidly varying hydrogen-derived water vapor signal. Dampening may be achieved in various manners. In one embodiment, a gas dryer (e.g., a Nafion® sulfonated tetrafluoroethylene based fluoropolymer-copolymer membrane gas dryer) may be employed. Various additional techniques may be employed to enhance such embodiments. For example, the hydrogen-derived water vapor signal may be rapidly modulated to further facilitate separation from the ambient water vapor signal. Likewise, the sample gas may be pre-humidified to a predetermined level to erase any memory of actual ambient water vapor and ensure a constant, stable ambient water vapor signal that can be readily separated out.

Another challenge is that the sample gas (e.g., atmospheric air) often includes hydrocarbon and other hydrogen bearing molecules that may convert to water vapor in the chemical conversion. This alternative source of water vapor may create an interfering signal. Such interfering signal may be significant in high sensitivity applications (e.g., for concentrations of hydrogen below 1 part per million (ppm)) or in environments with unusually large concentrations of hydrogen bearing molecules.

In various embodiments described herein, this challenge may be addressed by suppressing hydrogen bearing molecules in the sample gas by trapping (e.g., using a filter material, membrane, molecular sieve, cryogenic trap and/or other techniques) or tuning the chemical conversion to selectively oxidize hydrogen while avoiding conversion of hydrogen bearing molecules to water vapor. Alternatively, this challenge may be addressed by measuring hydrogen bearing molecule concentrations, calculating an amount of hydrogen bearing molecule-derived water vapor, and subtracting out the hydrogen bearing molecule-derived water vapor.

It should be understood that a variety of additional features and embodiments may be implemented other than those discussed in this Summary. This Summary is intended simply as a brief introduction to the reader for the further description that follows, and does not indicate or imply that the features and embodiments mentioned herein cover all aspects of the disclosure, or are necessary or essential parts of the disclosure.

BRIEF DESCRIPTION OF THE DRAWINGS

The description refers to the accompanying drawings of example embodiments, of which.

DETAILED DESCRIPTION OF ILLUSTRATIVE EMBODIMENTS

Figure 1A:
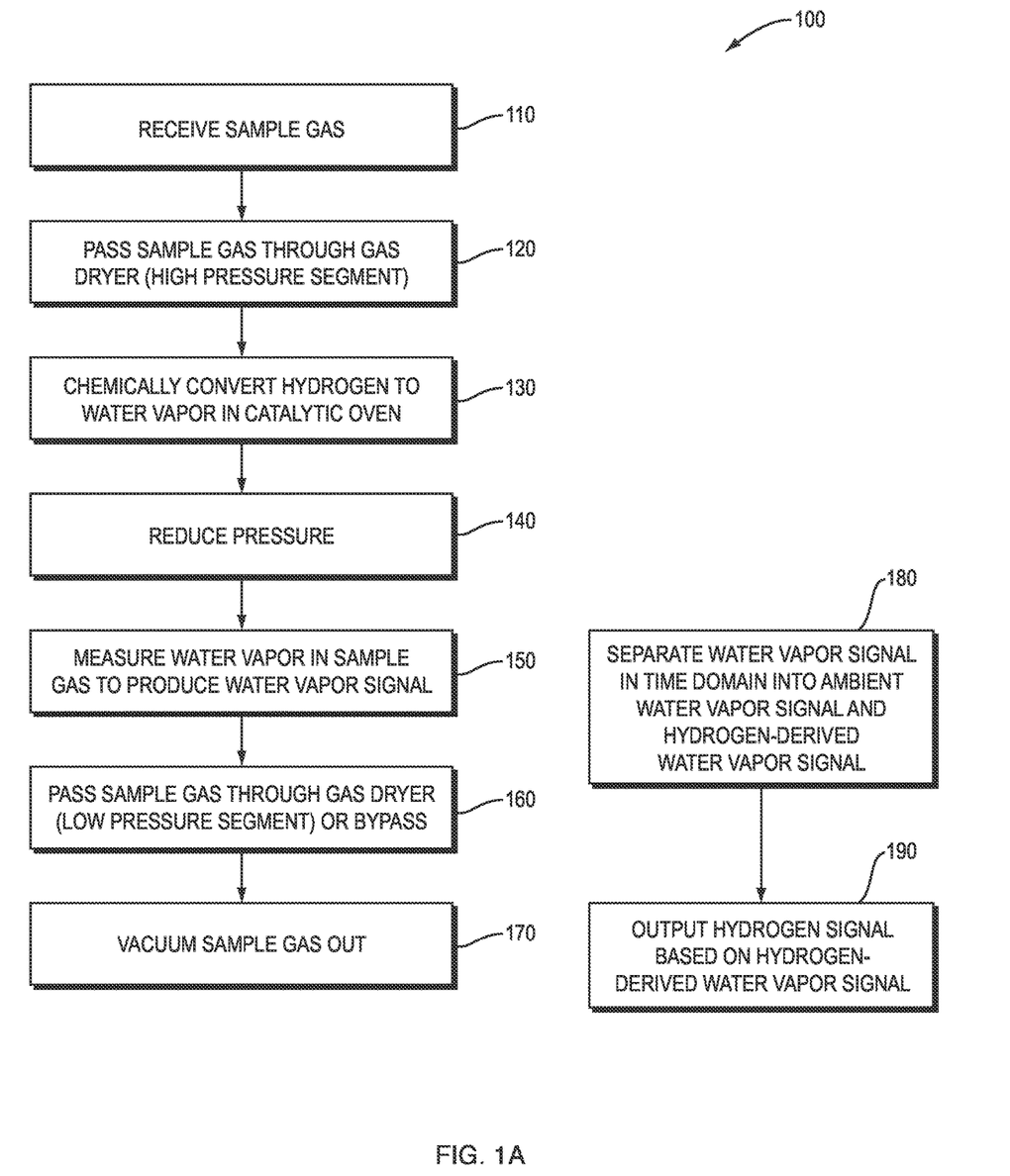
FIG. 1A is a flow diagram of an example sequence of steps for detecting molecular hydrogen according to a first embodiment.
Figure 1B:
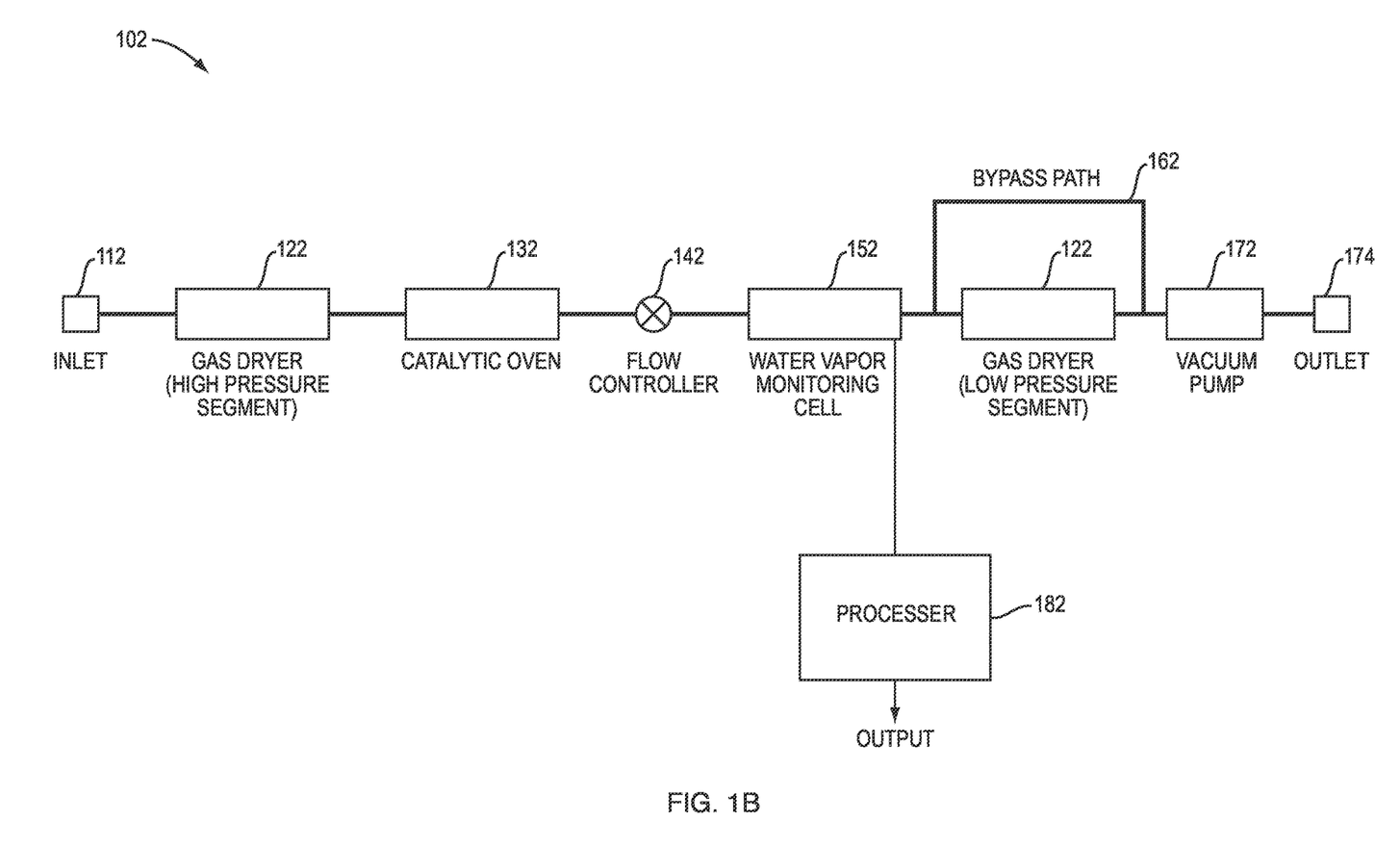
FIG. 1B is a block diagram of an example hydrogen detector with components that may implement the sequence of steps in FIG. 1A.

FIG. 1A is a flow diagram of an example sequence of steps 100 for detecting molecular hydrogen according to a first embodiment. FIG. 1B is a block diagram of an example hydrogen detector 102 with components that may implement the sequence of steps 100 in FIG. 1A. At step 110, an inlet 112 of the hydrogen detector 102 receives sample gas (e.g., atmospheric air) that includes ambient water vapor, molecular hydrogen and potentially hydrogen bearing molecules (including methane and non-methane hydrocarbons (NMHCs)). Ambient water vapor in the sample gas may vary, typically falling between 10,000 and 20,000 ppm for atmospheric air. Hydrogen bearing molecules in the sample gas are typically present in far smaller quantities, typically being about 3 ppm for atmospheric air (methane usually accounting for about 2 ppm and NMHCs accounting for the remaining 1 ppm). Absent a hydrogen source (e.g., a hydrogen leak), hydrogen typically is found at about 0.5 ppm in atmospheric air. A simple implementation of the hydrogen detector 102 may be suited for detecting hydrogen concentrations of about 1 ppm to about 40,000 ppm (i.e., the lower explosive limit of hydrogen). More complicated implementations of the hydrogen detector (e.g., that account for the potential presence of hydrogen bearing molecules in the sample gas) may be capable of specifically detecting sub-1 ppm concentrations.

At step 120, the sample gas from the inlet 112 is passed through a gas dryer 122, or more specifically a high-pressure segment thereof. In one implementation the gas dryer 122 is a Nafion® sulfonated tetrafluoroethylene based fluoropolymer-copolymer membrane gas dryer. Alternatively, a variety of different types of gas dryer may be employed. The gas dryer 122 may remove some ambient water vapor from the sample gas. However, the primary purpose of the gas dryer 122 is not to remove ambient water vapor, but to instead dampen time response in ambient water vapor, while having little effect on hydrogen. As explained further below, the gas dryer 122 serves a role similar to a low pass filter in the field of electronics.

At step 130, sample gas from the gas dryer 122 (or more specifically the high-pressure segment thereof) is received at a catalytic oven 132, which chemically converts hydrogen in the sample gas to water vapor (i.e., oxidizes the hydrogen). The catalytic oven 132 may include a hot (e.g., 100 to 200° Celsius (C)) catalytic surface (e.g., a platinum (Pt) surface) that rapidly and quantitatively converts hydrogen to water vapor.

The gas dryer 122 and catalytic oven 132 may operate near atmospheric pressure. At step 140, the converted sample gas from the catalytic oven 132 is passed through a flow controller 142 that reduces pressure. The flow controller 142 may cause a pressure drop by limiting flow in various manners. In one implementation, the flow controller is a critical orifice that limits flow. In some cases (e.g., cases with 40,000 ppm or greater water vapor concentrations) condensation may be prone to occur between the catalytic oven 132 and the flow controller 142. To avoid condensation, this region may be maintained at an elevated temperature (e.g., 30° C. or greater). In one implementation, this elevated temperature may be achieved by placing the flow controller 142 very close to the catalytic oven 132 so that byproduct heat from the catalytic oven 132 maintains the elevated temperature.

At step 150, the converted sample gas from the flow controller 142 is received by a water vapor monitoring cell 152, which measures water vapor therein to produce a water vapor signal. The water vapor monitoring cell 152 may employ optical detection, for example, laser spectroscopy or non-dispersive infrared (NDIR) absorption spectroscopy. It should be understood, however, that other types of detection, including other types of optical detection, may be employed, and the water vapor monitoring cell 152 may include various types of devices, including other types of spectrometers.

Figure 1C:
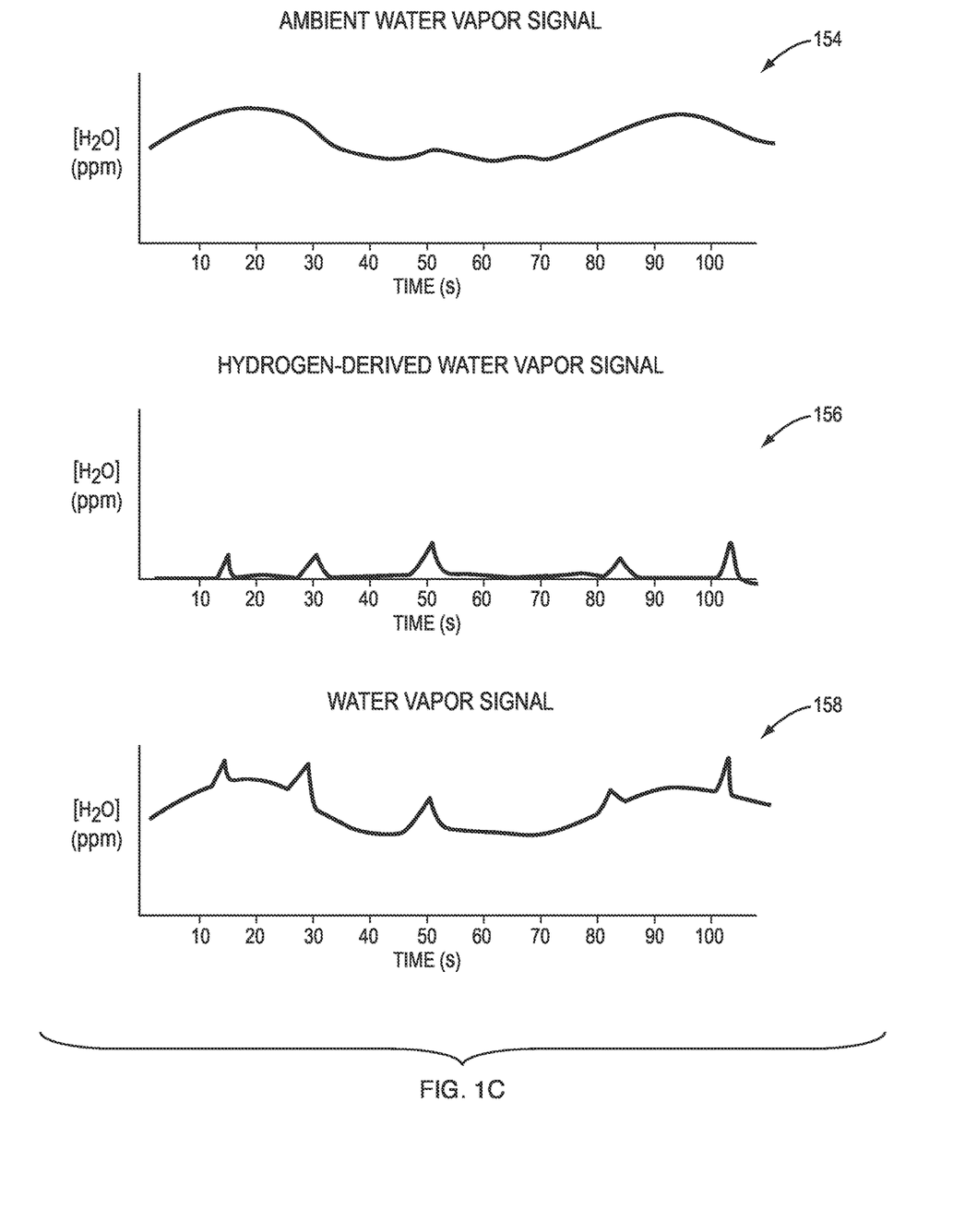
FIG. 1C is a set of graphs 154-158 illustrating an example water vapor signal, ambient water vapor signal and hydrogen-derived water vapor signal as a function of time.

The water vapor signal produced by the water vapor monitoring cell 152 includes two components in the time domain: a component derived from ambient water vapor referred to herein as the "ambient water vapor signal" and a component derived from converted hydrogen referred to herein as the "hydrogen-derived water vapor signal." FIG. 1C is a set of graphs 154-158 illustrating an example water vapor signal, ambient water vapor signal and hydrogen-derived water vapor signal as a function of time. The ambient water vapor signal often has a significant offset (e.g., 100 to 1000 pm) even after reduction by the gas dryer 122 due to the typically large (e.g., 10,000, 20,000 ppm, etc.) concentrations of ambient water vapor in atmospheric air, and typically only varies over long time periods (e.g., time periods greater than a minute). The ambient water vapor signal typically is relatively constant over short time periods (e.g., time periods of less than 1 second (s)) due to the dampening effects of the gas dryer 122. The hydrogen-derived water vapor signal typically has no significant offset due to the typically tiny (e.g., 0.5 ppm) concentrations of hydrogen in atmospheric air (absent a hydrogen source, such as a hydrogen leak). The hydrogen-derived water vapor signal may vary over short time periods (e.g., time periods of less than 1 s) since it is unaffected by the gas dryer 122.

It may be noted that any leaks in the system between the gas dryer 122 (or more specifically the high-pressure segment thereof) and the water vapor monitoring cell 152 may introduce water vapor changes that would not be dampened. Accordingly, special measures may be taken to minimize and/or eliminate potential leaks in this region (e.g., using high quality vacuum plumbing components in this region).

At step 160, the converted sample gas leaves the water vapor monitoring cell 152 and passes again through the gas dryer 122, or more specifically the low-pressure segment thereof. An optional bypass path 162 may also be provided to avoid the low-pressure segment.

At step 170, the converted sample gas passes through a vacuum pump 172 that pulls the sample gas through the hydrogen detector 102 and out an outlet 174.

In parallel, at step 180, the water vapor signal from the water vapor monitoring cell 152 is received by a processor 182 that separates the water vapor signal in the time domain into the ambient water vapor signal and the hydrogen-derived water vapor signal, for example, using digital signal processing (DSP) techniques. The processor 182 determines a hydrogen signal that describes molecular hydrogen in the sample gas based on the hydrogen-derived water vapor signal. In some implementations, the hydrogen-derived water vapor signal may be simply used as the hydrogen signal. In more complicated implementations, a conversion process may be employed to account for sources or errors or other factors.

Finally, at step 190, the processor 182, outputs the hydrogen signal, for example, storing it in a memory, passing it to another instrument, using it to generate a display in a user-interface of the hydrogen detector 102 itself, etc.

Figure 2A:
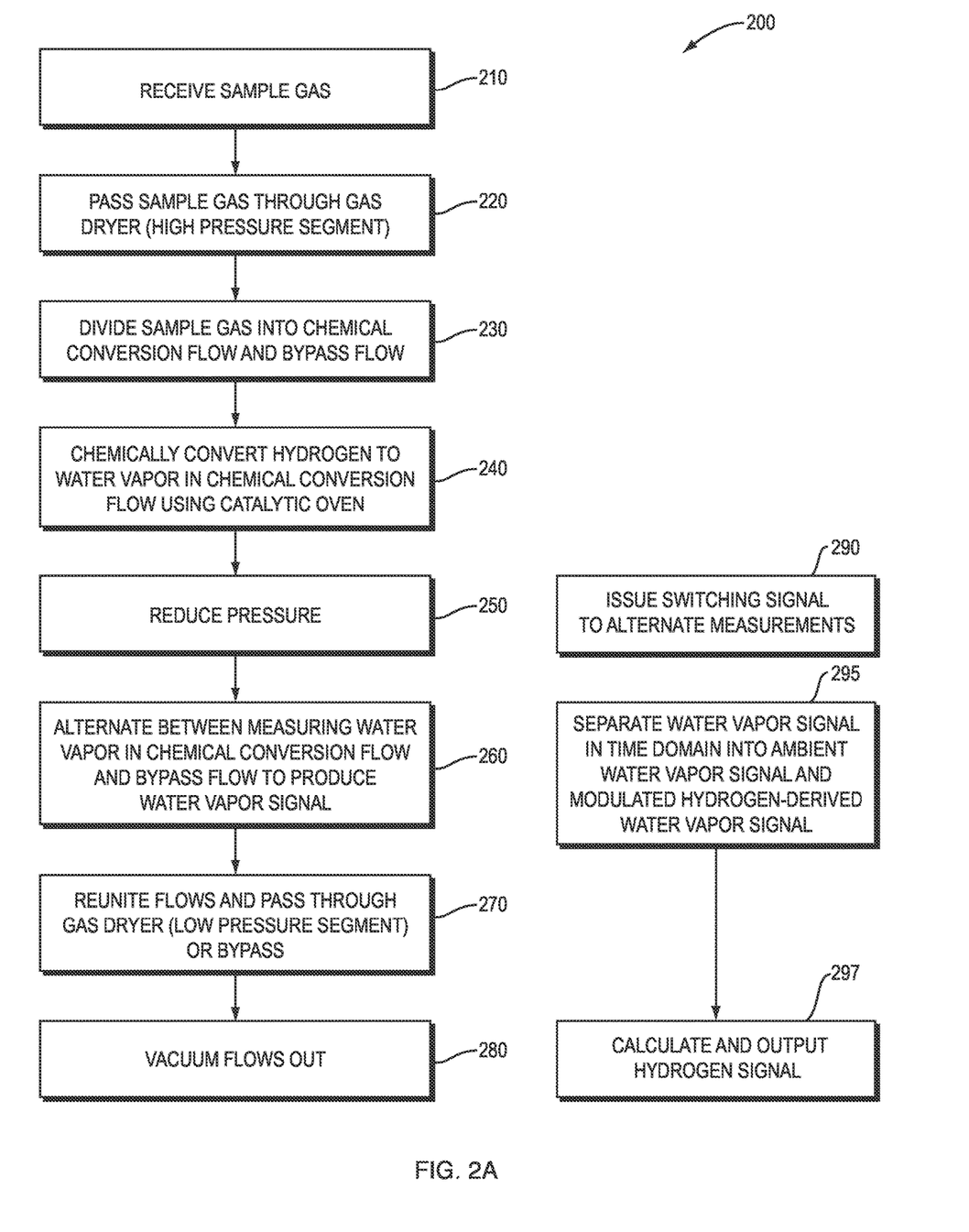
FIG. 2A is a flow diagram of an example sequence of steps for detecting molecular hydrogen according to a second embodiment.
Figure 2B:
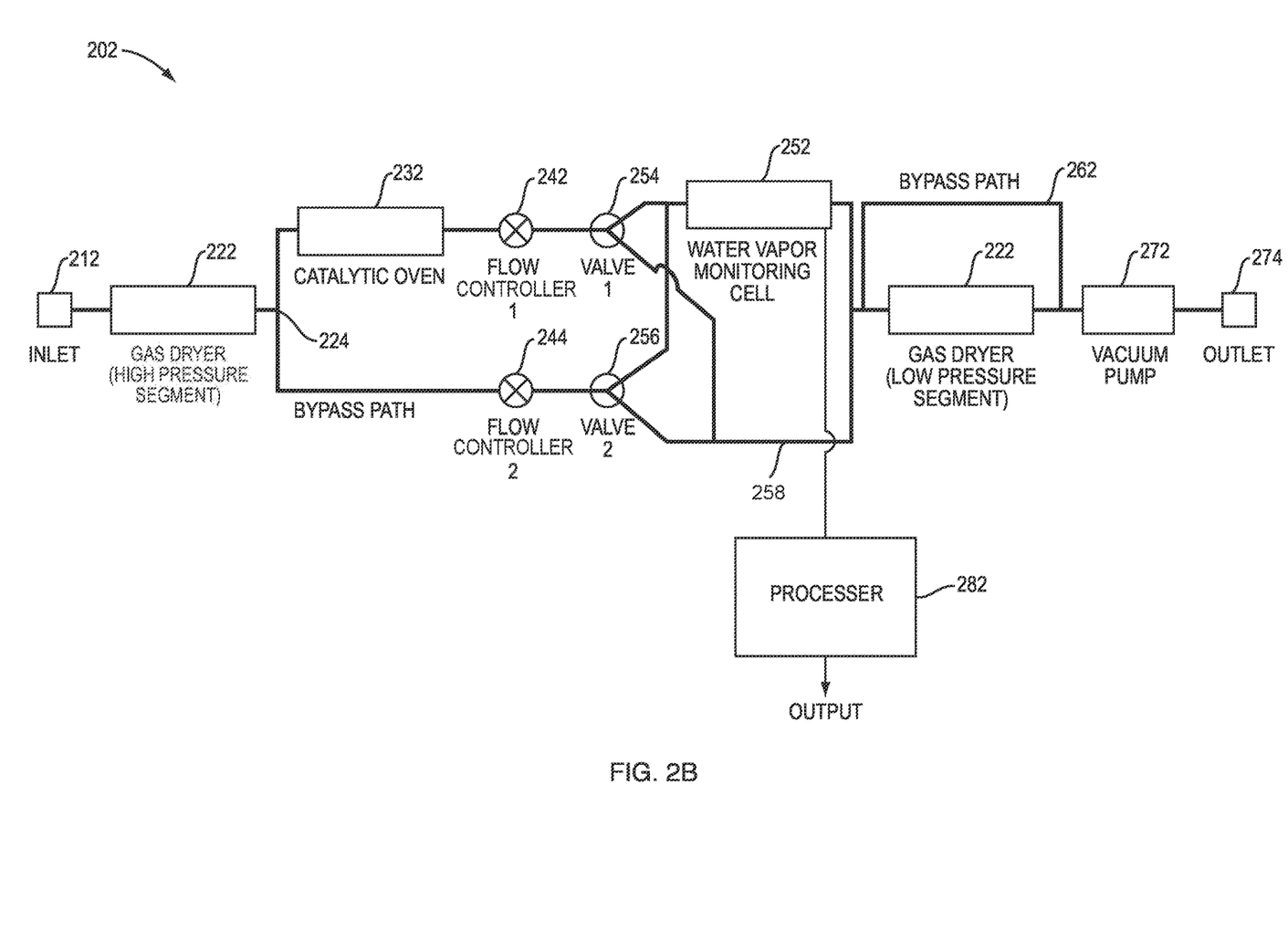
FIG. 2B is a block diagram of an example hydrogen detector with components that may implement the sequence of steps in FIG. 2A.

Performance of the example hydrogen detector 102 discussed in relation to FIGS. 1A-1B may be improved by actively modulating the hydrogen-derived water vapor signal. FIG. 2A is a flow diagram of an example sequence of steps 200 for detecting molecular hydrogen according to a second embodiment. FIG. 2B is a block diagram of an example hydrogen detector 202 with components that may implement the sequence of steps 200 in FIG. 2A. Where the steps and components of FIGS. 2A-2B are similar to those of FIGS. 1A-1B they will be discussed again only briefly, and the reader is referred to the above discussion for more detail.

At step 210, an inlet 212 of the hydrogen detector 202 receives sample gas (e.g., atmospheric air) that includes ambient water vapor, molecular hydrogen and potentially hydrogen bearing molecules (including methane and NMHCs).

At step 220, the sample gas from the inlet 212 is passed through a gas dryer 222, or more specifically a high-pressure segment thereof. Again, the gas dryer 222 may be a Nafion® sulfonated tetrafluoroethylene based fluoropolymer-copolymer membrane gas dryer or another type of dryer, and its primary purpose may be to dampen time response of ambient water vapor, while having little effect on hydrogen.

At step 230, sample gas from the gas dryer 222 (or more specifically the high pressure segment thereof) is passed to a flow divider 224 that divides the sample gas in half, creating a first flow that is passed to the catalytic oven 232 and that is referred to herein as the "chemical conversion flow," and a second flow that bypasses the catalytic oven 232 and that is referred to herein as the "bypass flow."

At step 240, the catalytic oven 232 chemically converts hydrogen in the chemical conversion flow to water vapor. Again, the catalytic oven 232 may include a hot (e.g., 200° C.) catalytic surface (e.g., a Pt surface) that rapidly and quantitatively converts hydrogen to water vapor. The gas dryer 222 and catalytic oven 232 may operate near atmospheric pressure.

At step 250, the chemical conversion flow from the catalytic oven 232 is passed through a first flow controller 242 that reduces its pressure, and the bypass flow is passed through a second flow controller 244 that reduces its pressure. Again, to avoid water condensation these regions may be maintained at an elevated temperature (e.g., 30° C. or greater).

At step 260, the water vapor monitoring cell 252 alternates between measuring water vapor in just the chemical conversion flow and in just the bypass flow to produce the water vapor signal. Again, the water vapor monitoring cell 252 may employ optical detection, for example, laser spectroscopy or NDIR absorption spectroscopy. To alternate measurement, first and second valves (e.g., electronically-controlled three-way valves) 254, 256 may be employed. In one implementation, the first valve 254 receives the chemical conversion flow from the first flow controller 242 and directs it either to the water vapor monitoring cell 252 (in its resting state) or to a bypass 258 around the water vapor monitoring cell 252 (in its activated state). The second valve 256 receives the bypass flow from the second flow controller 244 and directs it either around the water vapor monitoring cell 252 (in its resting state) or to the water vapor monitoring cell 252 (in its activated state).

In parallel steps, at step 290, a processor 282 is configured to issue a switching signal (e.g., a square wave) to the first and second valves 254, 256 to activate and deactivate them. The arrangement may maintain flow through the water vapor monitoring cell 252 and the bypass 258 around the water vapor monitoring cell 252 at all times, while alternating between the vapor monitoring cell 252 measuring water vapor in the chemical conversion flow or in the bypass flow. Provided the first and second valves 254, 256 are switched simultaneously, pressure in the vapor monitoring cell 252 will not significantly change, avoiding transient signals from the switching process itself. Further, flow rates through the water vapor monitoring cell 252 and the bypass 258 around the water vapor monitoring cell 252 need not be perfectly matched since their sum is constant and that will guarantee a nearly constant pressure in the water vapor monitoring cell 252.

Again, the water vapor signal produced by the water vapor monitoring cell 252 includes two components in the time domain: an ambient water vapor signal and a hydrogen-derived water vapor signal. However, the above discussed flow switching will modulate the hydrogen-derived water vapor signal making it easier to separate. The more rapid the switching signal to the valves 254, 256, the more rapid the modulation and the easier the separation (provided the switching signal is still less (e.g., 10× less) than a measurement rate of the water vapor monitoring cell 252 to ensure resolution). In one embodiment, the switching signal is greater than 1 Hertz (Hz) (e.g., a 2 Hz square wave).

Figure 2C:
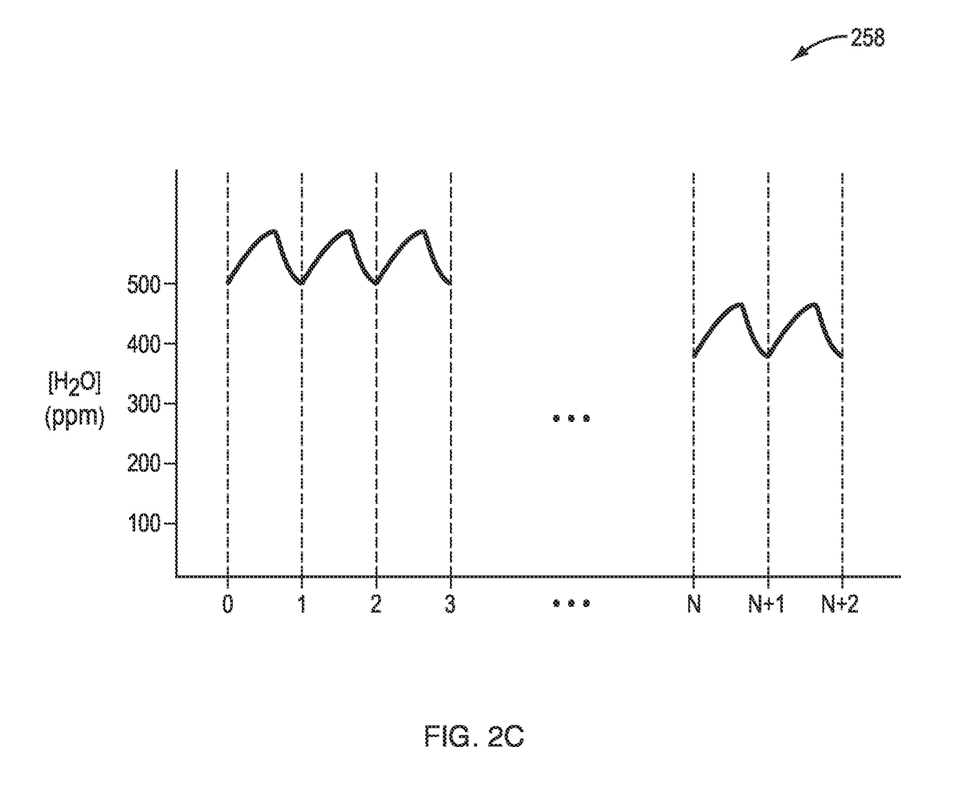
FIG. 2C is a graph illustrating an example water vapor signal having a hydrogen-derived water vapor component that has been rapidly modulated.

FIG. 2C is a graph 258 illustrating an example water vapor signal having a hydrogen-derived water vapor component that has been rapidly modulated. In this example, the rapidly modulated hydrogen-derived water vapor component corresponds to about 50 ppm of hydrogen and rides upon an ambient water vapor component that begins around 500 ppm and slowly decreases to about 400 ppm. The hydrogen-derived water vapor signal component is well separated in the time domain from the ambient water vapor component. In an idealized system, one would expect a 50 ppm square wave riding upon the ambient water vapor component. However, due to mixing and surface effects in real-world implementations, a damped square wave is more typical.

At step 270, the flows are reunited and both again pass through the gas dryer 222 (or more specifically the low-pressure segment thereof). An optional bypass path 262 may also be provided to avoid the low-pressure segment.

At step 280, the reunited flows pass through a vacuum pump 272 that pulls everything through the hydrogen detector 202 and out an outlet 274.

In parallel, at step 295, the water vapor signal from the water vapor monitoring cell 252 is received by the processor 282, which separates the water vapor signal in the time domain into the ambient water vapor signal and the modulated hydrogen-derived water vapor signal. The processor 282 determines a hydrogen signal that describes molecular hydrogen in the sample gas based on the modulated hydrogen-derived water vapor signal. In a simple implementation, while ignoring dampening of the modulation, the hydrogen signal can be determined as:

$$[H2]=[H2O]_{cc}-[H2O]_{bp}$$

where $[H2O]_{cc}$ is water vapor concentration measured when monitoring the chemical conversion flow and $[H2O]_{bp}$ is water vapor concentration measured when monitoring the bypass flow. In more complicated implementations, DSP techniques may be used. For example, the processor 282 may implement a digital lock-in amplifier to account for distortion caused by dampening effects. Any ambient water vapor fluctuations that are not completely suppressed by the gas dryer 222 will not be phase coherent with the modulation frequency and thereby can readily be suppressed.

Finally, at step 297, the processor 282 outputs the hydrogen signal, for example, storing it in a memory, passing it to another instrument, using it to generate a display in a user-interface of the hydrogen detector 202 itself, etc.

Operation of the various embodiments may be improved with various enhancements. In some enhanced embodiments, ambient water vapor fluctuations may be further suppressed by humidifying the sample gas to a predetermined relative humidity (e.g., 99%) using a humidifier (not shown in FIG. 1B or 2B) prior to passing the sample gas through the gas dryer 122, 222. Humidifying the sample gas to a predetermined relative humidity will erase memory of the actual ambient water vapor concentration. The gas dryer 122, 222 will reduce water vapor to a constant, stable level such that the ambient water vapor signal will not significantly vary even if actual ambient water vapor varies.

In further enhanced embodiments, hydrogen bearing molecules (including methane and NMHCs) in the sample gas that could be converted to water vapor and thereby produce an interfering signal are addressed. In some enhanced embodiments, hydrogen bearing molecules are suppressed by trapping using filter materials, membranes, molecular sieves, cryogenic traps and/or other trapping components. The trapping components may include pre-filters that reduce water vapor and carbon dioxide concentrations (e.g., to <1 ppm) to avoid saturation of the components intended to capture hydrogen bearing molecules. In some implementations, trapping components may be disposed between the gas dryer 122, 222 and the water vapor monitoring cell 152, 252. While trapping may be used with methane, trapping may be particularly well suited for suppressing hydrogen NMHCs since they are much stickier than hydrogen and are usually present in low concentrations.

In further enhanced embodiments, the catalytic oven 132, 232 may be tuned to selectively oxidize hydrogen while avoiding conversion of hydrogen bearing molecules to water vapor. Selective oxidation may be particularly well suited for suppressing methane since methane is relatively more difficult to oxidize than hydrogen, and thereby parameters may be selected for the catalytic oven 132, 232 that substantially oxidize one but not the other.

In still further enhanced embodiments, hydrogen bearing molecules in the sample gas may be compensated for by measuring hydrogen bearing molecule concentrations in the sample gas, calculating an amount of hydrogen bearing molecule-derived water vapor based on the measured hydrogen bearing molecule concentrations, and subtracting out hydrogen bearing molecule-derived water vapor from the water vapor signal. Compensation-based techniques may be particularly well suited for addressing methane.

Such measurements used in compensation-based techniques may be collected, for example, by adapting the techniques of FIGS. 2A-2B. Total methane concentration may be measured in the bypass flow (e.g., using a methane gas detector (not shown in FIG. 2B)). In the chemical conversion flow, methane concentration that survives passage through the catalytic oven 232 is also measured (e.g., again using a methane gas detector (not shown in FIG. 2B)). The difference between the total methane concentration and the surviving methane concentration indicates the quantity of methane oxidized in the catalytic oven 232. The processor 282 may determine a hydrogen signal that describes molecular hydrogen in the sample gas by subtracting out water vapor derived from methane oxidization. Each oxidized methane molecule will produce two water molecules, whereas oxidized hydrogen molecules will produce one water molecule. Accordingly, in a simple implementation, the hydrogen signal can be determined as:

$$[H2]=([H2O]_{cc}-[H2O]_{bp})-2*([CH4]_{bp}-[CH4]_{cc})$$

where $[H2O]_{cc}$ is water vapor concentration measured when monitoring the chemical conversion flow, $[H2O]_{bp}$ is water vapor concentration measured when monitoring the bypass flow, $[CH4]_{cc}$ is methane concentration in the chemical conversion flow, and $[CH4]_{bp}$ is methane concentration in the bypass flow. In more complicated implementations, the hydrogen signal can be determined using DSP techniques (e.g., a digital lock-in amplifier) to account for distortion caused by dampening effects.

In summary, the above description provide example techniques for rapid, sensitive detection of molecular hydrogen. It should be understood that various adaptations, modifications, and extensions may be made to suit various design requirements and parameters. For example, the techniques may be extended to determine hydrogen eddy covariance flux. An anemometer may be added to the hydrogen detector 102, 202 to measure air movement. The processor 182, 282 may be adapted to determine hydrogen eddy covariance flux based on correlation between the measurement of air movement and the water vapor signal.

Above all it should be understood that the above descriptions are meant to be taken only by way of example and the invention is not limited to the specific details of the example embodiments disclosed. What is claimed is:

What is claimed is:

1. A method for detecting molecular hydrogen, comprising:
  receiving sample gas that includes ambient water vapor and hydrogen;
  drying the sample gas to dampen variation in the ambient water vapor in the sample gas;
  dividing the sample gas into a chemical conversion flow and a bypass flow;
  chemically converting hydrogen in the chemical conversion flow to water vapor;
  alternating between measuring water vapor in the converted chemical conversion flow or the bypass flow to produce a water vapor signal;
  separating the water vapor signal into components based on differing variation over time to extract a hydrogen-derived water vapor signal from the water vapor signal; and
  outputting a hydrogen signal that describes molecular hydrogen in the sample gas based on the hydrogen-derived water vapor signal.

2. The method of claim 1, wherein the measuring water vapor is performed in a water vapor monitoring cell, and the alternating maintains constant flow through the water vapor monitoring cell.

3. The method of claim 2, wherein the constant flow through the water vapor monitoring cell has a constant pressure.

4. The method of claim 1, wherein the measuring is performed at a measurement rate and the alternating is performed at a switching rate that is at least 10 times less than the measurement rate.

5. The method of claim 1, wherein the drying is performed by a sulfonated tetrafluoroethylene based fluoropolymer-copolymer membrane gas dryer and the chemically converting is performed by heating the sample gas in a catalytic oven.

6. The method of claim 1, wherein the measuring water vapor is performed by optically detecting water vapor using laser spectroscopy or non-dispersive infrared (NDIR) absorption spectroscopy.

7. The method of claim 1, further comprising:
humidifying the sample gas to a predetermined relative humidity prior to passing the sample gas through the gas dryer.

8. The method of claim 1, further comprising:
suppressing hydrogen bearing molecules in the sample gas by trapping the hydrogen bearing molecules using at least one of a filter material, membrane, molecular sieve, or cryogenic trap.

9. The method of claim 1, further comprising:
suppressing hydrogen bearing molecules in the sample gas by tuning the chemical conversion to selectively oxidize hydrogen while avoiding conversion of hydrogen bearing molecules to water vapor.

10. The method of claim 1, further comprising:
compensating for hydrogen bearing molecules in the sample gas by measuring hydrogen bearing molecule concentrations in the sample gas, calculating an amount of hydrogen bearing molecule-derived water vapor based on the measured hydrogen bearing molecule concentrations, and subtracting out hydrogen bearing molecule-derived water vapor from the water vapor signal.

11. A molecular hydrogen detector, comprising:
an inlet configured to receive sample gas that includes ambient water vapor and hydrogen;
a gas dyer having a segment configured to receive sample gas from the inlet and to dampen variation in the ambient water vapor in the sample gas;
a flow divider configured to divide the sample gas into a chemical conversion flow and a bypass flow;
a catalytic oven configured to chemically convert hydrogen in the chemical conversion flow to water vapor;
one or more valves configured to alternately pass the converted chemical conversion flow or the bypass flow;
a water vapor monitoring cell configured to alternately measure water vapor in the converted chemical conversion flow or the bypass flow to produce a water vapor signal; and
a processor configured to separate the water vapor signal into components based on differing variation over time to produce an ambient water vapor signal and a hydrogen-derived water vapor signal, and to output a hydrogen signal based on the hydrogen-derived water vapor signal to describe molecular hydrogen in the sample gas.

12. The molecular hydrogen detector of claim 11, wherein the one or more valves comprise:
a first valve configured to selectively direct the chemical conversion flow to either the water vapor monitoring cell or to bypass the water vapor monitoring cell; and
a second flow valve configured to selectively direct the bypass flow to either the water vapor monitoring cell or to bypass the water vapor monitoring cell,
wherein the processor is configured to activate and deactivate the first valve and the second valve to cause the water vapor monitoring cell to alternately measure water vapor in the converted chemical conversion flow or the bypass flow.

13. The molecular hydrogen detector of claim 11, wherein the one or more valves are configured to maintain constant flow through the water vapor monitoring cell.

14. The molecular hydrogen detector of claim 11, wherein the water vapor monitoring cell is configured to measure water vapor in the converted chemical conversion flow or the bypass flow at a measurement rate and the one or more valves are configured to alternately pass the converted chemical conversion flow or the bypass flow at a switching rate that is at least 10 times less than the measurement rate.

15. The molecular hydrogen detector of claim 11, wherein the gas dryer comprises a sulfonated tetrafluoroethylene based fluoropolymer-copolymer membrane gas dryer and the water vapor monitoring cell comprises a laser spectrometer or a non-dispersive infrared (NDIR) absorption spectrometer.

16. The molecular hydrogen detector of claim 11, further comprising:
a humidifier disposed between the inlet and the gas dryer and configured to bring the sample gas to a predetermined relative humidity.

17. The molecular hydrogen detector of claim 11, further comprising:
a filter material, membrane, molecular sieve, or cryogenic trap configured to suppress hydrogen bearing molecules in the sample gas.

18. The molecular hydrogen detector of claim 11, further comprising:
a monitor configured to measure hydrogen bearing molecule concentrations in the sample gas,
wherein the processor is configured to compensate for hydrogen bearing molecules in the sample gas by calculating an amount of hydrogen bearing molecule-derived water vapor based on the measured hydrogen bearing molecule concentrations and subtracting out hydrogen bearing molecule-derived water vapor from the water vapor signal.

19. A molecular hydrogen detector, comprising:
means for receiving sample gas that includes ambient water vapor and hydrogen;
means for drying the sample gas to dampen variation in the ambient water vapor;
means for dividing the sample gas into a chemical conversion flow and a bypass flow;
means for chemically converting hydrogen in the chemical conversion flow to water vapor;
means for alternating between measuring water vapor in the converted chemical conversion flow or the bypass flow to produce a water vapor signal; and
means for separating the water vapor signal into components based on differing variation over time to extract a hydrogen-derived water vapor signal, and for outputting a hydrogen signal based on the hydrogen-derived water vapor signal to describe molecular hydrogen in the sample gas.

20. The molecular hydrogen detector of claim 19, wherein the means for dividing is configured to maintain constant flow through the water vapor monitoring cell.

* * * * *